United States Patent
McGregor

(10) Patent No.: US 8,583,686 B2
(45) Date of Patent: Nov. 12, 2013

(54) SYSTEM, METHOD AND COMPUTER PROGRAM FOR MULTI-DIMENSIONAL TEMPORAL DATA MINING

(75) Inventor: Carolyn Patricia McGregor, Brooklin (CA)

(73) Assignee: University of Ontario Institute of Technology, Ottawa, Ontario (CA)

( * ) Notice: Subject to any disclaimer, the term of this patent is extended or adjusted under 35 U.S.C. 154(b) by 0 days.

(21) Appl. No.: 13/386,151

(22) PCT Filed: Jul. 22, 2010

(86) PCT No.: PCT/CA2010/001148
§ 371 (c)(1),
(2), (4) Date: Mar. 15, 2012

(87) PCT Pub. No.: WO2011/009211
PCT Pub. Date: Jan. 27, 2011

(65) Prior Publication Data
US 2012/0166484 A1    Jun. 28, 2012

Related U.S. Application Data

(60) Provisional application No. 61/227,660, filed on Jul. 22, 2009.

(51) Int. Cl.
G06F 17/30    (2006.01)

(52) U.S. Cl.
USPC ............ 707/776; 707/748; 707/737; 701/29; 705/3

(58) Field of Classification Search
USPC .................. 707/776, 748, 737; 701/29; 705/3
See application file for complete search history.

(56) References Cited

U.S. PATENT DOCUMENTS

| | | | | |
|---|---|---|---|---|
| 7,693,697 | B2 * | 4/2010 | Westenskow et al. | 703/11 |
| 7,716,155 | B2 * | 5/2010 | Aggarwal | 706/58 |
| 7,844,899 | B2 * | 11/2010 | Boucher | 715/266 |
| 7,970,772 | B2 * | 6/2011 | Aggarwal et al. | 707/748 |
| 8,280,899 | B2 * | 10/2012 | Lo et al. | 707/763 |
| 2004/0024773 | A1 * | 2/2004 | Stoffel et al. | 707/102 |
| 2007/0226212 | A1 * | 9/2007 | Aggarwal et al. | 707/6 |
| 2010/0030418 | A1 * | 2/2010 | Holland | 701/29 |
| 2010/0076785 | A1 * | 3/2010 | Mehta et al. | 705/3 |

* cited by examiner

Primary Examiner — Debbie Le
(74) Attorney, Agent, or Firm — Lorelei Greta Graham

(57) ABSTRACT

The present invention provides a system, method and computer program for multi-dimensional temporal abstraction and data mining. The invention comprises collecting and optionally cleaning multi-dimensional data, the multi-dimensional data including a plurality of data streams; temporally abstracting the multi-dimensional data; and relatively aligning the temporally abstracted multi-dimensional data based on a shared time point of interest.

23 Claims, 7 Drawing Sheets

Figure 5.12: CRISP-DM extended for Clinical Practice and Research (Heath 2006)

SYSTEM, METHOD AND COMPUTER PROGRAM FOR MULTI-DIMENSIONAL TEMPORAL DATA MINING

FIELD OF THE INVENTION

The present invention relates generally to data mining. The present invention relates more specifically to data mining environments that enable multi-dimensional, time dependent queries and analysis.

BACKGROUND OF THE INVENTION

There are numerous areas where multiple devices generate multiple data streams, and it is desirable to monitor, analyze and/or predict behavior that is time dependent. This time dependency, across multiple data streams can be difficult to resolve, particularly for the purposes of analysis, using existing data mining environments.

There is a need for an improved data mining environment that enables data analysis (including for data mining purposes) of time dependent data across, for example multiple streams, multiple entities, multiple possible attributes of the entities, multiple possible behaviors of the data stream over time and multiple events reflected in the data stream, resulting in a multi-dimensional environment (i.e. entities, streams, entity attributes, stream behaviors and stream events). There is a further need for such a data mining environment that is flexible enough to permit relatively open ended queries thereby enabling for example the detection of trends, including trends with new dimensions or based on relatively small data sets.

For example, intensive care units worldwide use a range of medical monitoring equipment, such as medical devices for life support and critical monitoring. These devices have been operational for over 50 years and enable critically ill medical and surgical patients to be observed and treated in a complex, specialized environment by physicians and nurses trained in restoring and/or maintaining the function of vital organs. A diverse range of devices display physiological data and many have the ability to output this data via serial, USB or other ports.

In addition to collecting this data for use in real-time by care providers, it is desirable to enable secondary analysis of the data for other related clinical research, for example, to enable the discovery of previously unknown trends and patterns that may be indicative of the onset of some condition. The potential for the secondary use of health data, such as this, is significant. In an American Medical Informatics Association White Paper published in the Journal of the American Medical Informatics Association in 2007, entitled "Toward a National Framework for the Secondary Use of Health Data", the urgency for infrastructures to support the secondary use of data in today's data intensive healthcare environment is seen as pivotal to the US Health system.

Medical monitoring equipment produces large amounts of data, which makes analyzing this data manually impossible. Adding to the complexity of the large datasets is the nature of the physiological monitoring data—the data is multi-dimensional, where it is not only changes in individual dimensions that are significant, but sometimes simultaneous changes in several dimensions. As the time-series produced by the monitoring equipment is temporal, there is a need for clinical research frameworks that enable both the dimensionality and temporal behavior to be preserved during data mining, so as not to lose the information of time and context during the mining process.

In the field of clinical research, to enable the discovery of new trends and patterns that may be indicative of the onset of a condition in intensive care patients where the timing of certain events in a patient's condition can be of high importance, there is a need for integrated temporal abstraction data mining systems to include methods to enable realignment of historical data in relation to the onset of the condition being investigated.

SUMMARY OF THE INVENTION

The present invention provides a system, method and computer program for multi-dimensional temporal data mining.

The present invention also provides a method for multi-dimensional temporal abstraction and data mining, the method comprising: collecting and optionally cleaning multi-dimensional data, the multi-dimensional data including a plurality of data streams; temporally abstracting the multi-dimensional data; and relatively aligning the temporally abstracted multi-dimensional data based on an at least one time point of interest.

The system consists of a computer implemented data mining system characterized by: an at least one data store; and a processor in communication with the at least one data store, the processor configured to: collect and construct from the data store an at least one time dependent data set using selection criteria set by a user; apply temporal abstractions to the at least one time dependent data set in accordance with pre-defined abstraction rules to produce an at least one temporally abstracted data set; and re-align the at least one temporally abstracted data set relative to an at least one time point of interest to produce an at least one relatively aligned data set.

The computer program of the present invention consists of a computer readable medium having stored thereon a computer program for data mining, the computer program comprising a set of instructions for generating and storing a plurality of accessible information files when used with a processor, the set of instructions comprising a method characterized by: constructing an at least one time dependent data set using selection criteria set by a user; applying temporal abstractions to the at least one time dependent data set in accordance with pre-defined abstraction rules to produce an at least one temporally abstracted data set; relatively aligning the at least one temporally abstracted data set relative to a time point of interest to create an at least one relatively aligned data set; and storing each at least one data set for subsequent retrieval.

In this respect, before explaining at least one embodiment of the invention in detail, it is to be understood that the invention is not limited in its application to the details of construction and to the arrangements of the components set forth in the following description or the examples provided therein, or illustrated in the drawings. The invention is capable of other embodiments and of being practiced and carried out in various ways. Also, it is to be understood that the phraseology and terminology employed herein are for the purpose of description and should not be regarded as limiting.

DETAILED DESCRIPTION

Overview

Figure 1:
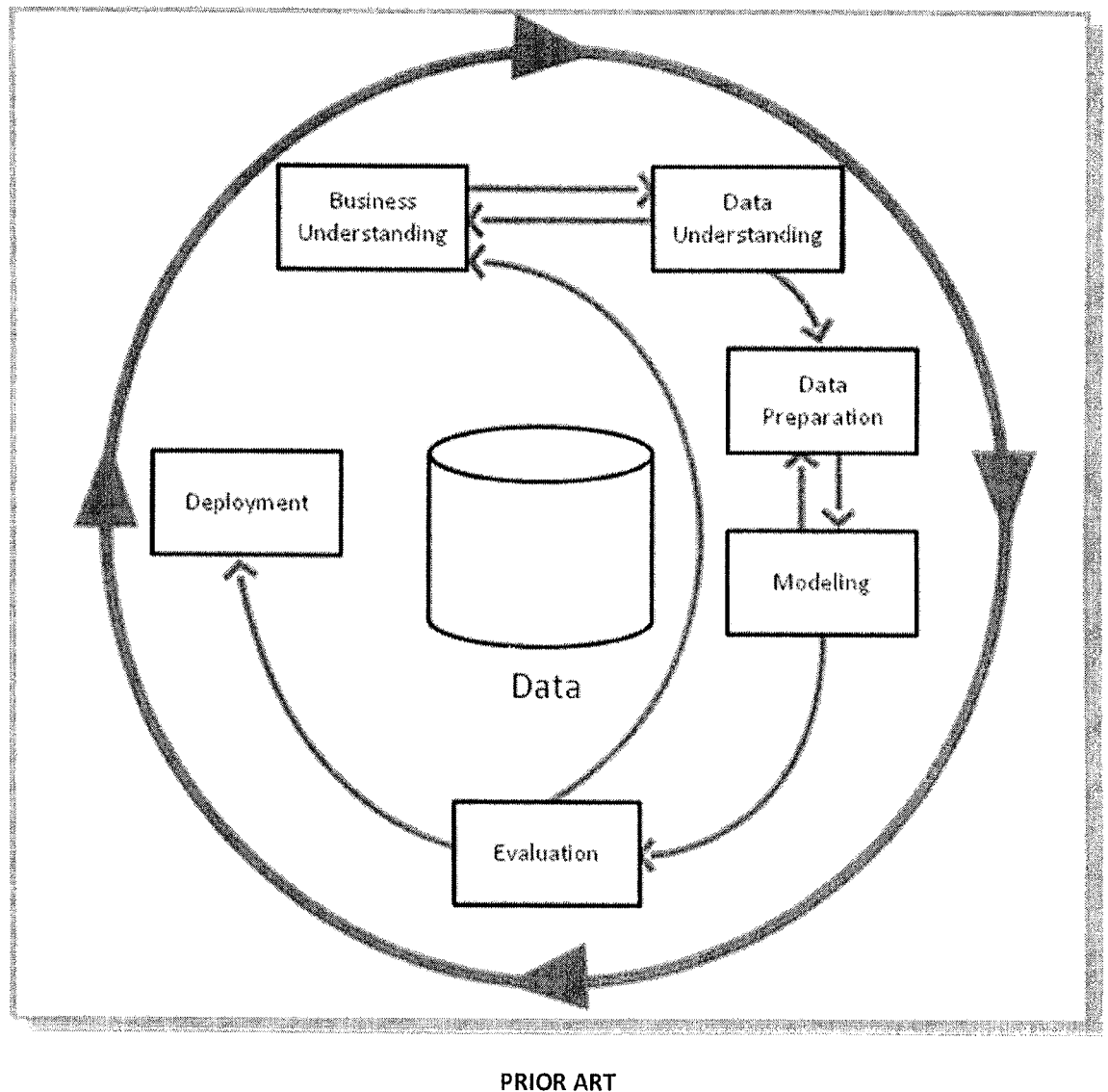
FIG. 1 illustrates a CRISP-DM model of the prior art.
Figure 2:
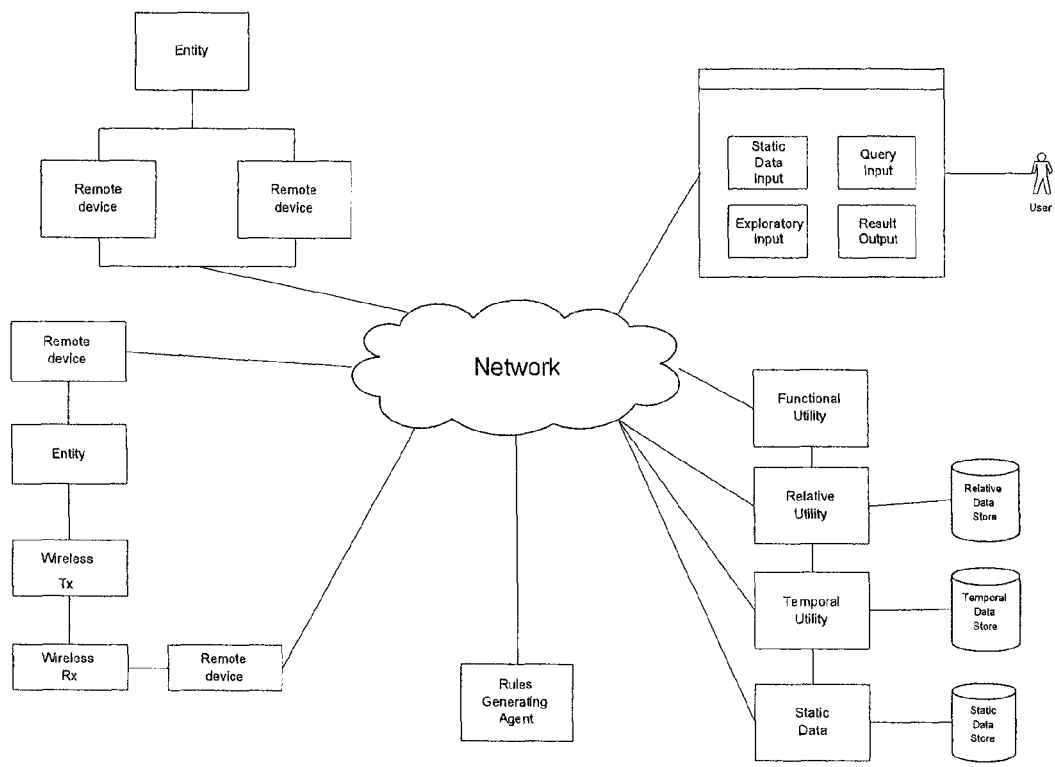
FIG. 2 illustrates a system for implementing the present invention.

The present invention relates to an improvement on known multi-dimensional data mining environments. The invention includes the addition to a data mining environment of a series of temporal and relative rules. A particular advantage provided by the invention is that the temporal rules enable a multi-dimensional environment that by means of a data preparation stage, enables data streams to be encoded with time stamps relative to specific points of interest. This environment provides a holistic framework where multiple studies across multiple parameters for multiple patients are possible.

The method of the present invention includes a number of steps. First, the multi-dimensional data is collected and optionally cleaned up. Second, the multi-dimensional data is temporally abstracted, creating a dynamic data mining environment in multiple dimensions (as further detailed below). Third, the temporally abstracted data is relatively aligned.

The process of temporal abstraction takes either raw device or pre-processed stream data as input and utilizes domain knowledge (context) to translate the raw data into behavior or event information that is at a slower frequency of time than the inputted stream(s) for the inputted data thereby producing higher level, context-sensitive, qualitative, interval-based representations. Complex temporal abstractions can be created by assessing behaviors across multiple streams.

Optionally, the fourth step is to engage in exploratory and/or explanatory data mining in the created multi-dimensional data mining environment. Exploratory data mining refers to data mining by supporting queries to the data mining environment without imposing rules or functions. Explanatory data mining attempts to further validate rules by performing further data mining on more datasets.

An alternative fourth step, or a fifth step in addition to the fourth step described above, is linking to one or more remote devices to enable the one or more remote devices to use the resulting temporally abstracted and relatively aligned data. The remote devices could be any device linked to or associated with the invention that provides the data streams described. The remote devices may be located in close physical proximity of each other, the system and the entity. The remote devices may alternatively be located outside of close proximity to the system, each other, or the entity for example at remote regions of a country or the world, connected to the system over the Internet or another network. The remote devices could be linked to the system or to entities wirelessly.

The devices could all be connected to one entity, or a series of subsets of devices could be connected to a series of entities existing within an overall population or sample set. Devices could be for example medical physiological monitoring devices, smart meters, car telemetry monitoring devices, weather sensors, network traffic monitors, share price data streams or power plant monitoring systems. Matching entities within a population could be patients within a healthcare population, homes within an electricity grid, motor vehicles, or weather stations respectively.

The computer program of the present invention is best understood as including (1) a temporal utility or agent, and (2) a relative utility or agent, both corresponding to the method steps above. The temporal utility and the relative utility are linked. The computer program of the present invention enables at the very least queries to the resulting temporally abstracted and relatively aligned data. Optionally, the computer program enables exploratory and/or explanatory data mining, which in one implementation takes the form of the functional agent that has been described.

Optionally, a rules generating agent is provided. The rules generating agent provides a mechanism for a user to either generate rules by proposing rules and storing them in a data table or to store rules proposed by the system during the exploratory data mining stage. Alarms, alerts or messages can be initiated in response to the temporally abstracted and relatively aligned data with respect to the rules.

The process may be user driven. Typically, the user will know what they are studying and the rules that are desired. Queries may be user driven in that a user may manipulate, analyze or monitor data as desired. The queries may be provided by the user using a user interface.

The user interface may provide means for inputting study selection criteria. This part of the user interface is data driven and enables the user to select criteria to define the relative time point of interest together with other selection criteria for the entities that will qualify for the study.

The user interface may also provide means for inputting relative time points of interest, which enables the user to select points of interest based on either: an event; an entity attribute; a stream behavior; or a stream event (with the latter two being represented by their own stream temporal abstractions). A user may first determine whether the time point of interest is from an event, entity attribute or a temporal abstraction. The time point of interest may be defined as a datetime, which is a time point operable to be used as the reference point to relatively align the data streams of interest. Based on the user's selection, the user is then provided with a list populated directly from the database that is either: a list of possible events; a list of entity attributes that have datetimes; or a list of temporal abstractions. In the case of temporal abstractions the user can choose whether the first or most recent occurrence of the temporal abstraction is of interest and may also determine whether the start or end time is of interest.

If an event is chosen as the relative point of interest then the datetime that the event occurred for a selected entity is the relative time point.

If an entity attribute that is a datetime is chosen as the relative point of interest (for example, what common behaviors exist after a certain time relative to the entity), then that datetime is the relative time point for the selected entity such as the date of completion of manufacture or the date of birth.

If a temporal abstraction is chosen, then the datetime associated with the selection criteria for the temporal abstraction for the given entity is chosen.

The result is a list of entities that satisfy the selection criteria and for each entity the datetime point representing $t_0$ for the relative alignment process is also listed. This resultant list may be persistently stored within the database, but this is not compulsory as it can be regenerated via the information contained within the other tables based on the contents of the study table for that particular study.

In addition to defining the relative time point of interest, the user is able to provide other selection and/or exclusion criteria through similar database populated data driven lists to determine what entities should be part of the study. These criteria can be from any or all of the entity attributes, event attributes, temporal abstractions or relative temporal abstractions.

Queries can be made on the static and/or raw data stream together with the temporal and relative data streams in any desired combination. The temporally abstracted and relatively aligned data can also be dynamically analyzed to determine specific information. For example, one could easily determine average performance at a specific point of time, which is very difficult to do manually, particularly where concurrent stream assessment is required.

The system of the present invention can be implemented to a known database engine or similar technology. The invention may comprise a computer system that includes one or more computers including at least the temporal utility and the relative utility, the computer system being linked to one or more database engines or similar technologies, the database engine(s) either including static data, data from one or more remote devices or sensors, or the computer system being linked to one or more remote devices or sensors, directly or indirectly, so as to populate the one or more databases provided by the database engine(s) with sensor data.

Figure 3:
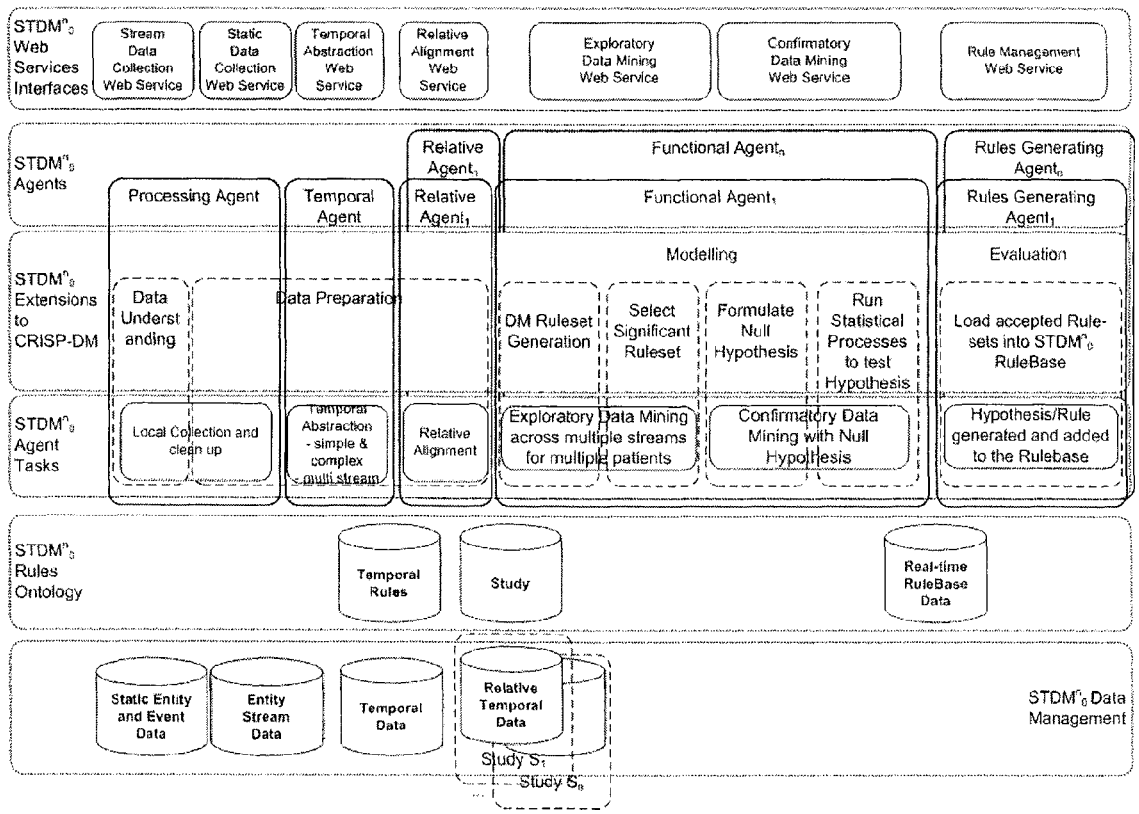
FIG. 3 illustrates the present invention accessible through a cloud computing architecture.

Optionally, the system can be implemented as a cloud computing implementation where the use of this environment is provided as an external service through a series of web services. FIG. 3 illustrates the present invention accessible through a cloud computing architecture. The system could also be implemented as a proprietary solution still accessible via the set of web services where data from one source (and possibly multiple sensors, etc. from each source) is provided to a web server connected to the Internet and linked to at least the temporal utility and the relative utility where the web server delivers the temporally abstracted and relatively aligned data, or output of the exploratory and/or explanatory data mining discussed above. Rules as provided by the present invention could also be added, changed or deleted from using a web service. It should be noted that one of the benefits of the web service model is that multiple organizations linked to the web server can provide a larger number of data sets that improves the data accessible by each of the participating organizations.

The invention is particularly applicable to a variety of areas, specifically wherever there are multiple sensors or otherwise multiple streams of data relating to events or behaviors occurring and different times that relate to a specific "end state" or "end condition" of an "entity" that is of interest. An "entity" could be a patient or an apparatus being monitored, for example. The events or behaviors may cause or contribute to the end state or end condition, for example, a series of successive events may define a timeline leading to a particular state or condition.

This environment includes an approach to data mining that supports null hypothesis testing through the provision of exploratory and confirmatory data mining functions. The invention also includes an ontology design to support the temporal, relative rules together with a multi-dimensional rule base. The environment supports static data (for example, clinical data) together with sensor data that can be numeric data (for example, temperature or blood pressure) streams or waveform data (for example, ECG and EEG) streams and supports data mining that cross correlates between data streams together with the static data. The storage of temporal and relative temporal data is also supported for secondary analysis of the data for other related clinical research.

In terms of the area of application, it is important to understand that the invention can be applied to any domain where there may be multiple sensors used to monitor events or parameters that relate to similar or the same behavior. The technology is relevant at least to patient care, monitoring structural failure, weather events, smart meters, etc. Wherever it is a challenge to extrapolate from multiple sources of information, over multiple events that occur at different times, the invention is advantageous.

Also advantageously, the multi-dimensional data mining environment of the present invention supports multiple studies. These can be entity centric, entity attribute centre, stream centric, or event centric, or can also draw from any other fields in the ontology. For example, in the field of patient care, three babies may all develop an infection and, for example, the technique enables the investigation of common factors between these three cases, for example as to heart rate, respiratory rate, etc. Additionally, as there are actual times associated with these incidents, the invention enables tracking of multiple behaviors on multiple streams generated by the various sensors, and building a data structure that enables realignment relative to a diagnosis event in order to engage in better analysis within the environment, for example to better track progress of each baby in real time based on average factors at a particular point in time during the progression of the infection, etc.

The present invention enables a user to have advanced knowledge of when to intervene to prevent or mitigate a condition. There is an event state of interest, for example an engine failure or diagnosis event. The present invention provides an environment where the user can see the previous events that move toward an event state, and to explore that trajectory path to determine where the entity is in terms of event state (i.e. is the entity heading for the event state or not, and when). The trajectory path may be defined based on averages that are historical, but enables a user or a system to react in real time.

Furthermore, the present invention enables the trajectory path to be created using relatively small data sets and to be refined based on additional data sets. The present invention also reacts to new conditions.

In a particular illustrative example, the data can be temporally abstracted relative to an event. For example, where a condition or event has occurred, there are multiple sensors providing a picture of a particular entity, for example a patient or a car. These multiple sensors may be on different organs or components for example, thereby providing a multi-dimensional data stream. Data can be collected over an extended period. Data from similar entities in which the condition or event occurred can also have been collected over time. The condition or event can be set as a point of interest, and the multi-dimensional data can be mined to determine trends leading to the condition or event.

The paper entitled "*Multi-Dimensional Temporal Abstraction and Data mining of medical Time Series Data Trends and Challenges*", Catley, C, Stratti, H & McGregor, C, August 2008, *Multi-Dimensional Temporal Abstraction and Data Mining of Medical Time Series Data: Trends and Challenges,* 30$^{th}$ International IEEE Engineering in Medicine and Biology Society Conference, 4322-5 illustrates some of the current research on time series data, temporal abstraction generally (as opposed to the particular temporal abstraction techniques and system described herein), as well as principles of null hypothesis testing.

One aspect of the invention is population of the data mining environment for health care applications with physiological data. This can be done for example using the physiological data models described in "A Web Service Based Framework for the Transmission of Physiological Data for Local and Remote Neonatal Intensive Care", McGregor, C., Heath, J., & Wei, M., 2005, *Proceedings of the IEEE International Conference on e-Technology, e-Commerce and e-Service*, Hong Kong, IEEE pp 496-501.

Data Mining Framework

The present invention provides a framework for multi-dimensional data mining of temporal data. The present invention can supports both local use together with the use through a service based model. This framework is herein referred to as a service-based multi-dimensional temporal data mining ($STDM''_O$). The framework as applied to support analysis and trend detection in historical data from Neonatal Intensive Care Unit (NICU) patients is described in "A Multidimensional Temporal Abstractive Data Mining Framework", Bjering, H. & McGregor, C., 2010, *Proc. 4th Australasian Workshop on Health Informatics and Knowledge Management*, Brisbane, HIKM pp. 29-38, which is herein incorporated by reference. $STDM''_O$ is operable to discover trends and patterns indicative of the onset of a condition; includes methods for applying temporal abstraction across multiple parameters for multiple entities to enable mining of multi-dimensional temporal data; supports null hypothesis testing; can generate hypotheses that can be used by a real-time event stream processor analysing the current condition of entities; and generates hypotheses that can be translated into rules to be used by a real-time event stream processor used for monitoring and alerting.

Figure 7:
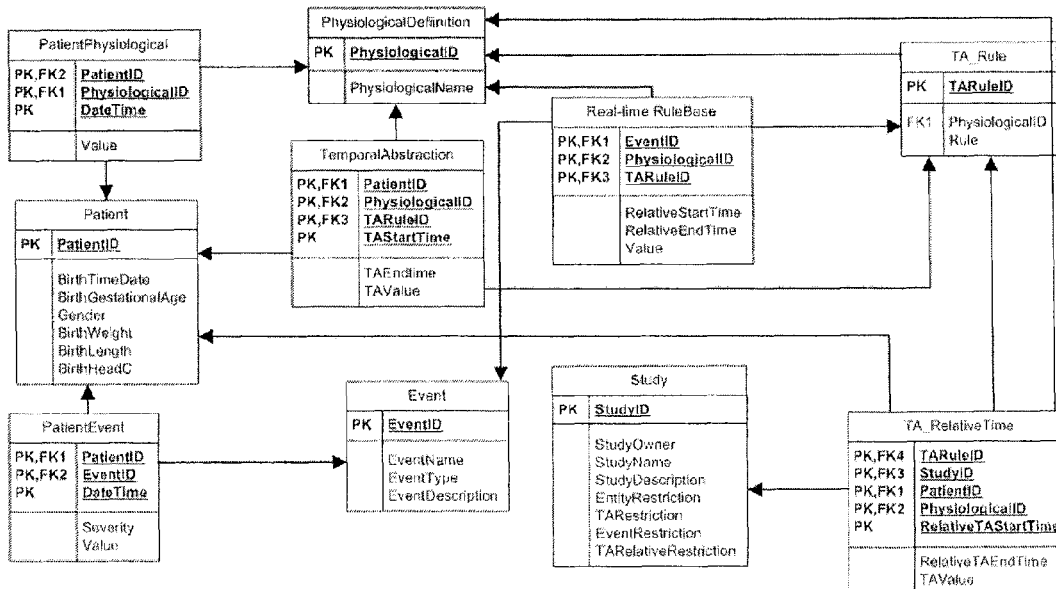
FIG. 7 illustrates the data storage schema of FIG. 6 particularly for implementing the $STDM''_0$ framework for clinical research.

$STDM''_O$ provides a mechanism to support the functionality of an extended CRISP-DM data mining model to facilitate null hypothesis testing. CRISP-DM is a 6 phase hierarchical process model as described in FIG. 1. At the highest level the six phases are: business understanding; data understanding; data preparation; modeling; evaluation and deployment. Each of these phases has associated with it a set of sub tasks that are spread across the lower levels of the hierarchical model as illustrated in FIG. 7. The approach to extend CRISP-DM to support the scientific method based null hypothesis testing incorporated in this invention is shown in a cloud computing model in FIG. 3.

$STDM''_O$ comprises an architecture that bridges the gap between data management and data mining research, enabling the secondary use of some of the vast amount of data collected by monitoring equipment. New data collected is fed into the framework with the existing data to help further refine the hypotheses created in the $STDM''_O$ framework.

The $STDM''_O$ model is supported by multiple agents that facilitate interaction between the user and the data contained in the active rules ontology and the data management layers. The multiple agents are comprised of a processing agent, temporal agent, a relative agent, functional agent, and a rules generating agent, as hereinafter described and as shown in FIG. 3.

A plurality of data stores are also provided by the $STDM''_O$ framework, including a temporal data store and a relative temporal data store.

The multi-agent data mining system of the $STDM''_O$ framework is illustrated in FIG. 3. This framework diagram maps the agents used to the appropriate parts of the extended CRISP-DM model and sets out the individual $STDM''_O$ tasks.

Referring to the horizontal column in FIG. 3 labelled $STDM''_O$ Agents, the first agent in the $STDM''_O$ framework is the processing agent. The processing agent acts as a pre-processor for the functional agent, performing the tasks of getting and preparing the data and storing it within the data stores so as to be ready for further processing by the temporal agent. As illustrated under the $STDM''_O$ Extensions to CRISP-DM column, the processing agent is used to support and partially support the phases of data understanding and data preparation within the CRISP-DM model.

Under the $STDM''_O$ Data Management column, the processing agent would usually acquire data from external databases for the static data and via sensor devices for the stream data.

The processing agent uses the static and stream web services enabling data to be pushed or pulled directly to the processing agent. Data can also be sent directly to the processing agent via a direct connection.

Referring next to the $STDM''_O$ Agent Tasks column of FIG. 3, there is one primary task performed by the processing agent, namely, local collection and cleanup. This task involves collecting the static and stream data from the external databases for use within the $STDM''_O$ framework, as the data arrives and general data cleaning, such as, checking for erroneous values is performed. Those erroneous values are those, for example, caused by irrelevant factors related to the entity, employing strategies for dealing with missing values, etc.

The data is extracted from external databases by the processing agent, transformed to the required format and stored in the data stores within the $STDM''_O$ framework, as set out in the $STDM''_O$ Data Management column. Static data obtained from the entity or describing the entity is entered into a static data table and the sensor data is stored in the sensor data table. This task supports all of the data understanding and part of the data preparation components of the extended CRISP-DM model proposed within $STDM''_O$.

The local collection and clean up task is the task of the processing agent as one of the agents within $STDM''_O$. Referring next to the $STDM''_O$ Web Services Interfaces column shown in FIG. 3, the processing agent can either acquire the data directly from the source or be provided the data by the Stream Data Collection Web Service and the Static Data Collection Web Service.

In a traditional data warehouse setting, where raw data is copied into the data warehouse and aggregated via a periodic load followed by batch aggregations, the processing agent can, for example, be implemented as an agent in the database management system (DBMS) housing the data warehouse. A periodic extract could run from the operational data receiving the sensor data and that extract loaded into the $STDM''_O$ environment via a script enacting the processing agent.

Within the stream computing paradigm, where data is manipulated as a stream as the data arrives in real-time, the processing agent could be a stream computing program receiving the streams directly from the sensors as the data arrives in real-time and outputting the data through a database output operator to enable the row insertion.

In a services computing paradigm, both the database script and the stream computing program can be enacted via the enactment of the Stream Data Collection Web Service or the Static Data Collection Service.

Referring again to the $STDM''_O$ Agents column, the next agent in the framework is the temporal agent. The temporal agent generates temporal abstractions on the data prepared and stored by the processing agent. The temporal abstractions to be performed are defined by temporal rules of the $STDM''_O$ Rules Ontology. The temporal abstractions represent a pre-processing method before data mining which allows the temporal aspects and the context of the data to be preserved.

By way of example, in a clinical research setting, for a given patient set each of the relevant physiological streams may be temporally abstracted into appropriate abstractions such as trends (increasing, decreasing) and level shifts (high, low). Each raw piece of data may belong to several abstractions. For example, a particular measurement may be part of an 'increasing' abstraction, and at the same time be within 'normal' limits. Complex abstractions can also be done across multiple abstracted parameters.

While individual data values themselves may not provide valuable information, when considered over time and context the values can create meaning. The $STDM''_0$ framework will use temporal abstraction as pre-processing of the data prior to exploratory data mining. In accordance with the tasks listed under the $STDM''_0$ Agent Tasks column, for each entity, each sensor stream is temporally abstracted into appropriate abstractions such as trends and level shifts. Complex abstractions can also be done across multiple abstracted parameters. Each abstraction including actual start and end times for the particular abstraction instance may be stored as temporal data as part of the $STDM''_0$ Data Management component As depicted by its overlap in FIG. 3 with the data preparation step, the temporal agent is used to partially support the phase of data preparation within the CRISP-DM model.

Referring next to the $STDM''_0$ Web Services Interfaces column, it is observed that the temporal agent uses the temporal abstraction web service enabling data to be pushed or pulled directly to the temporal agent. Data can also be sent directly to the temporal agent via a direct connection.

The temporal agent has five main functions performed as the temporal abstraction task: (1) retrieve the relevant temporal rules from a temporal rules table; (2) apply the temporal rules to the data, creating simple abstractions for individual data streams for individual entities; (3) store the created slow frequent temporal abstractions streams in the temporal data store; (4) create complex abstractions from the simple abstractions created in step 3, according to any of the relevant temporal rules; and (5) store any complex temporal abstractions streams created in the temporal data store.

Examples of temporal abstractions may include the following:
(i) Neonatal Intensive Care:
  1) The start and end times where mean arterial blood pressure falls below the neonatal patient's current gestational age;
  2) The start and end times where the neonatal patient's blood oxygen level falls below 85%;
  3) The start and end times where the neonatal patient's blood oxygen level is falling at a rate greater than the threshold specified; and
  4) A complex abstraction of the start and end times where 1) and 2) occur concurrently for more than 20 seconds.
(ii) Electricity Grids:
  1) The start and end times when electricity goes above a certain threshold.
(iii) Weather:
  1) The start and end times when the temperature at that weather station goes above 35° C.

Referring again to FIG. 3, the relative agent represents the next phase of the framework. When a user wishes to investigate the possibility of certain patterns or other signs appearing in an entity's sensor data before or after some event, there will often be a need for aligning the data, including both static data and abstractions of sensor data, relative to for example the time of diagnosis. This will allow users to study particular outcomes and remedial methods on other entities. These relative alignment processes make up the $STDM''_0$ Agent Tasks of the relative agent.

The point of interest to which to relatively align the data could be a time of diagnosis in a clinical context but need not be. It could be based on any event or behavior.

When researching a particular event, the abstractions are matched with the event table holding the entity's event time and date. This information is fed through a transform algorithm to enable a measurement in time for the abstractions relative to the point in time of the diagnosis. $T_0$ is the point of event, and $T_{-1}, T_{-2}, T_{-3} \ldots $ T-n indicates the distance in time between an abstraction before the time of event, and the event. This step enables the 'lining up' of data relating to entities at the point of the event, to enable the detection of trends and patterns that may be common in entities at a particular point in time before or after the onset of some event. Significant changes in a particular parameter in the lead up time to the event can be isolated to enable the finding of any significant indicators for determining what time the change or behavior of a particular parameter occurred in relation to the onset of the event.

The relative agent uses the abstractions created by the temporal agent and stored in the TemporalAbtraction table, together with static information of individual entities to create the data subset or data mart in support of a specific study. There can be any number of relative alignments performed on the temporal abstractions, as denoted by the Relative Agent$_1$ and Relative Agent$_n$ labels in FIG. 3. A particular alignment is determined by the type of study that is to be undertaken, which is specified in the Study table in the database.

The relative agent is designed to enable the relative alignment of entity data and temporal abstractions based on the study to be undertaken. The relative agent is used to realign the temporal abstractions, relative to some point in time of interest that is shared within the temporally abstracted data set, for example as the relative point in time for when an event was apparent for entities.

Many studies can be conducted on the same temporal abstractions, and the same temporal abstractions can be used for many different studies and may require realignment in several different ways. Each aligned temporal abstraction stored in the relative temporal data table will belong to a particular study. The realigned temporal abstractions will form the basis for the optional exploratory and confirmatory data mining performed in later stages of the process.

Studies can be created where no time adjustment occurs as a result of the relative alignment. In these cases, the relative alignment performs a subset selection of entities of interest based on the static information of individual entities.

The relative agent is used to partially support the phase of data preparation within the CRISP-DM model and represents the final step of data preparation for a given study.

Referring to the top horizontal column of FIG. 3, the relative agent uses the relative alignment web service enabling data to be pushed or pulled directly to the relative agent. Data can also be sent directly to the relative agent via a direct connection.

The relative agent has three main functions: (1) retrieve the relevant data and temporal abstractions from the temporal data store, based on the selection specifications given by the user; (2) apply the transformations specified for the study to be undertaken to the absolute timed temporal abstractions to create the set of aligned temporal abstractions, called relative abstractions, as time (start and end times) is relative to the alignment point; and (3) store the relatively aligned abstractions in the relative temporal data store to allow for further processing by the functional agent.

Example of relative alignment tasks may include the following:
(i) Neonatal Intensive Care:
1) Select all neonatal patients who were diagnosed with nosocomial infection and relatively align the data based on the data of suspected nosocomial infection and include data for the four days before and all days after the suspected nosocomial infection diagnosis.
2) Select all patients who were born at 23 weeks gestation and create a study set of data for those patients for the equivalent of their 27-29 gestational 27-29 weeks.
(ii) Electricity Grids:
2) Align meter data for weekend days where the temperature was >40 C for more than 4 hours the following day's temperature was <27 C and select the subsequent 72 hours of meter data (ie to detect a pattern of excessive air conditioner usage in the time following a very hot day in instances where it may not be required.

Again referring to FIG. 3, the next agent of the $STDM''_0$ framework is the functional agent. The functional agent attempts to detect and validate new trends and patterns in the relatively aligned temporal data and includes exploratory and confirmatory data mining. The initial analysis is done using exploratory data mining to enable the discovery of interesting rule sets to investigate further. Exploratory data mining is used to analyze the realigned temporal abstractions, created by the temporal and relative agents, across multiple data streams for multiple entities to explore the data in search of new trends and patterns that can be represented through rule set generation and also known as a hypotheses. The scientific method stages of "make observation" and "invent hypothesis to explain observation" are supported by the exploratory data mining. If a correlation within the data is found, then this can be validated using confirmatory data mining. The validation can be either via testing on further data sets or via the use of null hypothesis testing or both.

The purpose of the analysis is to look for level shifts and trends in temporal data and cross correlate data mining findings across multiple data streams for multiple entities in an attempt to detect previously unknown patterns that may exist in entities with a particular event, and thereby create new hypotheses that can possibly become new rules that can be applied in entity monitoring.

Temporal abstraction as performed in the previous step preserves the temporal aspect of the data, enabling this temporal aspect to be included when performing the exploratory data mining across multiple streams and for multiple entity tasks.

There exists the ability for the user to use alternate data mining techniques in this step; the framework does not restrict a selection of the data mining technique that best matches the mining task. The data mining technique selected must have an awareness of time series data. The result of the exploratory data mining is examined by the user, and significant rule-sets are selected.

Figure 4:
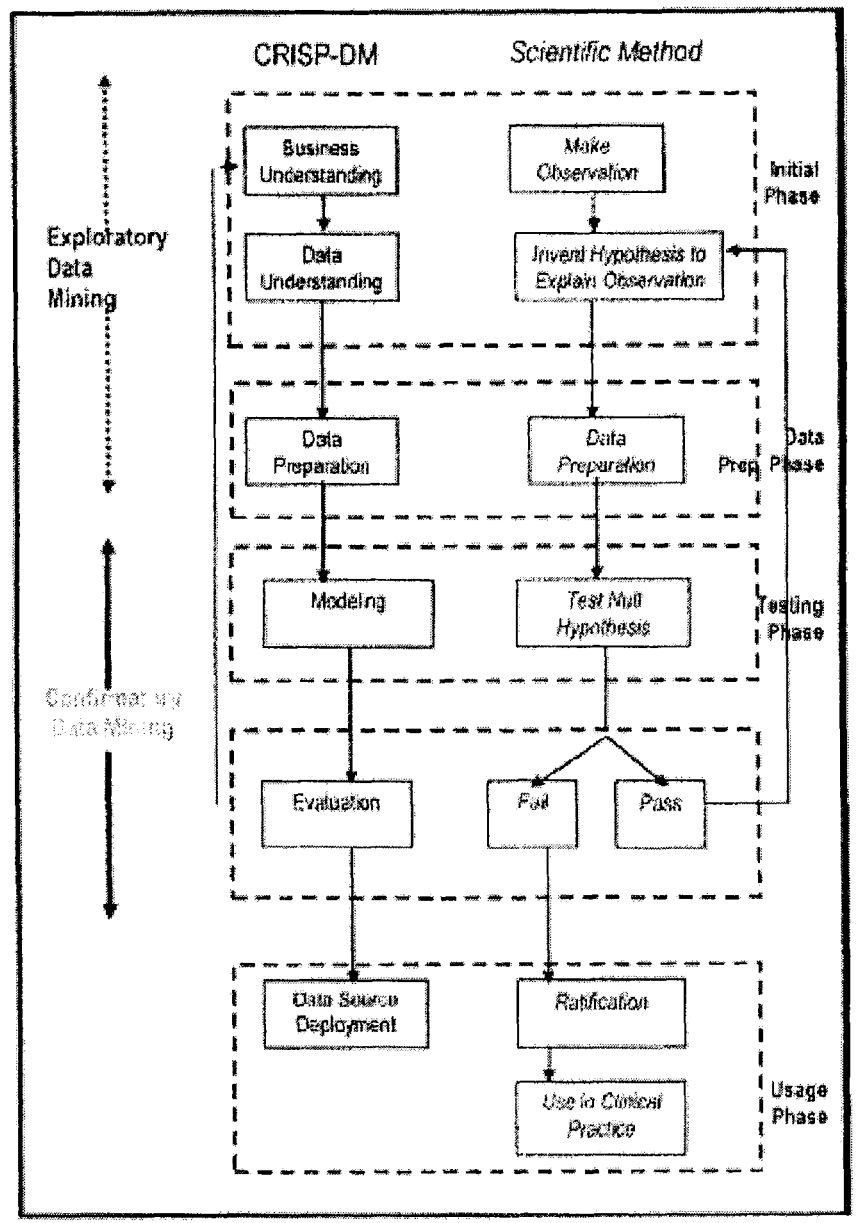
FIG. 4 illustrates a parallel between the known CRISP-DM and the scientific method.
Figure 5:
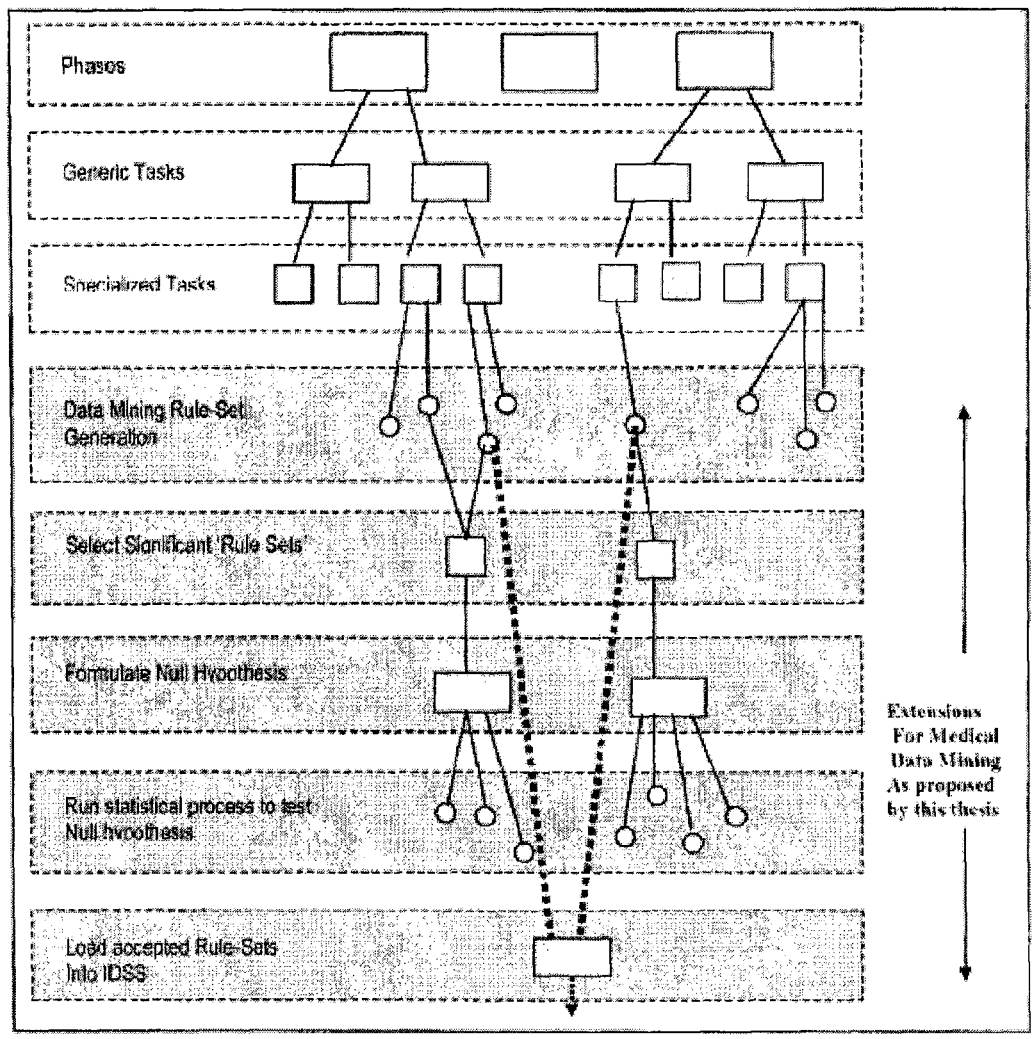
FIG. 5 illustrates an extended CRISP-DM model satisfying the need for null hypothesis testing.

The functional agent is used to support the phase of modelling within the CRISP-DM model. The $STDM''_0$ framework extends CRISP-DM to support the scientific method. The parallel between the known CRISP-DM and the scientific method is illustrated in FIG. 4

The $STDM''_0$ framework exploratory data mining task is part of the data mining rule-set generation and select significant rule sets phases of the extended CRISP_DM model. This task will be completed by the functional agent in the multi-agent framework.

Referring to the $STDM''_0$ agent tasks column, under the functional agent step, a subset of entities, as selected for a given study based on a given hypothesis, and their associated relatively aligned temporal streams can be used as a training set for exploratory data mining. Subsequently in explanatory mode the same hypothesis (without switching to null hypothesis mode) can be run on more data for other subsets of entities as originally selected for the given study or the whole subset that satisfies the study selection criteria for entities.

The incorporation of null hypothesis testing within $STDM''_0$ enables validation of the hypothesis through a confirmatory data mining process and represents an optional step for use within domains where further verification of the resultant rules are required such as but not limited to healthcare. This Confirmatory Data Mining with Null Hypothesis task is performed within the Formulate Null Hypothesis and Run Statistical Processes to test Hypothesis extensions to CRISP-DM. The hypothesis is translated from a hypothesis to a null hypothesis and the validation attempts to disprove the null hypothesis. If the disproving is unsuccessful then the hypothesis holds.

An example of the integration of a null hypothesis test is as follows:

Anecdotal clinical evidence suggests that the correlation of the following two events has a direct association with neonatal instability resulting in unstable heart rate: "Given a hypothetical newborn baby born 5 weeks premature (35 weeks gestational age), a fall in mean blood pressure less than 35 mm Hg (ie the numerical value of their gestational age) is clinically relevant. At all gestations a fall in peripheral oxygen saturation less than 85% for greater than 20 seconds is also clinically relevant."

The temporal agent prepares the initial simple temporal abstractions on mean blood pressure and blood oxygen saturation as per the above and a complex temporal abstraction is prepared to select segments when both occur concurrently. These are relatively aligned to heart rate instability episodes.

In this example, the exploratory data mining performed during the DM Rule Generation and Select Significant Ruleset steps by the Functional Agent results in a correlation that supports the anecdotal clinical evidence as above.

The Formulate Null Hypothesis step enables the representation of the ruleset as a Null Hypothesis.

For this example a correlation coefficient of 0.8 is used. This hypothesis is thus utilizing a correlation coefficient notation of the form:

$$H_1:\rho_{(X,Y)}>0.8$$

Where:
  X represents ECG instability and;
Y represents ABPmean<gestational age for 20 seconds; AND SaO2<85% for the same 20 seconds
The effective null hypothesis is represented as:

$$H_0:\rho_{(X,Y)}=0.8$$

The true null hypothesis is represented as:

$$H_0:\rho_{(X,Y)}<0.8$$

During the Run Statistical Processes to test Hypothesis step, set out under the $STDM''_0$ Extensions to CRISP-DM model, the null hypothesis is tested against further mixes of test sets to attempt to disprove the null hypothesis. If the null hypothesis can not be disproved, then the hypothesis is considered proven.

Optionally, exploratory and confirmatory data mining can be automated. Exploratory data mining can be automated with the system using in turn the time of an event, an entity attribute that represents a datetime point, or temporal abstraction start times to determine relative alignment points for entities that would qualify. Qualifying entities could be chosen iteratively based on restrictions based on entity attribute criteria, event attribute criteria temporal abstraction criteria and/or relative temporal abstraction criteria. Data mining could be automated to attempt to cluster entities based on common behaviors or via other data mining approaches return results where there are strong correlations.

For example, a user may optionally select some data streams or ones that make sense and then use those for further explanatory data mining. A user may choose to perform this step for example to input results that are known based on domain knowledge, to avoid additional system processing to discover known trends.

The functional agent uses the exploratory data mining and confirmatory data mining web services enabling data to be pushed or pulled directly to the functional agent. Data can also be sent directly to the functional agent via a direct connection.

Referring next to the rules generating agent vertical column of FIG. 3, the rules generating agent performs the task of adding the rules created as part of the rule set generation through the exploratory data mining within the functional agent into a rules format that can be represented in a manner to enable insertion into the rules table. A user may evaluate the rule set and decide if it is to be incorporated into the Real-time Rule Base as an active rule for intelligent entity monitoring.

As indicated in FIG. 3, this task is part of the evaluation phase in the extended CRISP-DM model.

Figure 8:
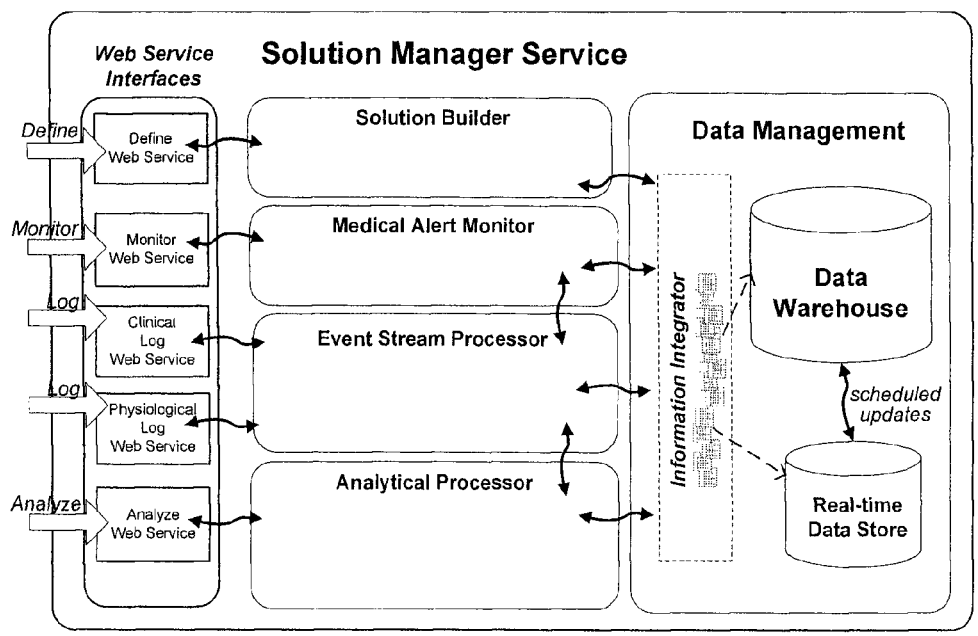
FIG. 8 illustrates a solution manager service for enabling clinicians to carry out the methods of the present invention.

These rules can be utilized by an event stream processor such as that detailed in the solution manager service in FIG. 8 for real-time event monitoring. An event stream processor may incorporate temporal abstraction on real-time data streams to allow the utilisation of temporally abstracted rules for alerting.

The rules generating agent uses the rule management web service enabling data to be pushed or pulled directly to the rules generating agent. Data can also be sent directly to the rules generating agent via a direct connection.

An extended CRISP-DM model satisfying the need for null hypothesis testing is illustrated in FIG. 4. The extended CRISP-DM model is used to support the data mining model in the $STDM''_0$ framework. This extension to the CRISP-DM model illustrates the incorporation of the null hypothesis testing component of the Scientific Method approach within the Confirmatory Data Mining Modelling and Evaluation components of the extended CRISP-DM model. The following sections detail the extended CRISP-DM implementation within the STDMn0 framework. In particular the extensions within the Modeling and Evaluation components.

Data Understanding

The data understanding phase involves various tasks associated with collection and familiarization with the collected data. The data is described and investigated, and any data quality problems are identified. The data understanding phase uses the services of the processing agent in the multi-agent system to complete part of the local collection and clean-up task in the $STDM''_0$ framework.

Data Preparation

The data preparation phase includes all action involved in transforming the initial unprocessed data into the final dataset to be fed into the data mining tools. It includes activities such as selecting and cleaning the data, constructing and integrating data sets and formatting the data to be ready for data mining. The data preparation phase uses the services of three agents in the multi-agent system. The processing agent finalizes the initial preparation started in the data understanding phase, ready for the temporal agent to perform the temporal abstractions on the temporal data, before the relative agent performs the relative re-alignment of the data in accordance with the study undertaken.

Modeling and Evaluation

The modelling phase includes selecting and applying modeling techniques. This phase includes data mining rule-set generation, select significant rule-set, formulate null hypothesis, and run statistical processes to test hypothesis. The Formulate Null Hypothesis and Run Statistical Processes to Test Null Hypothesis represent the STDMn0 framework implementation of the CRISP-DM extensions within the modelling and evaluation components to support the Test Null Hypothesis and Pass/Fail test within the Scientific Method. All the modelling and Evaluation phases are performed by the functional agents in the multi-agent system and are mapped to the $STDM''_0$ framework as described below.

Data Mining Rule-Set Generation and Select Significant Rule-Set

The data mining rule set generation phase is the phase where exploratory data mining is conducted. In the $STDM''_0$ framework exploratory data mining is performed on relatively aligned temporal abstractions, including multiple streams for multiple entities. The results of the exploratory data mining are used when moving to the select significant rule-set phase.

Formulate Null Hypothesis

The formulate null hypothesis phase uses the output of the select significant rule set phase, where significant rule sets are selected from the results of exploratory data mining. A null hypothesis is created for any results that indicate interestingness and further investigation.

Run Statistical Processes to Test Null Hypothesis

Another part of the modelling phase, run statistical processes to test null hypothesis phase follows the formulate null hypothesis phase. The run statistical processes to test null hypothesis phase performs the confirmatory data mining with null hypothesis task of the $STDM''_0$ framework, aiming to prove or disprove the null hypothesis.

Data Source Deployment

The Data Source Deployment component of the Extended CRISP-DM model is implemented through the functions of the Rules Generating Agent.

Data Storage

Figure 6:
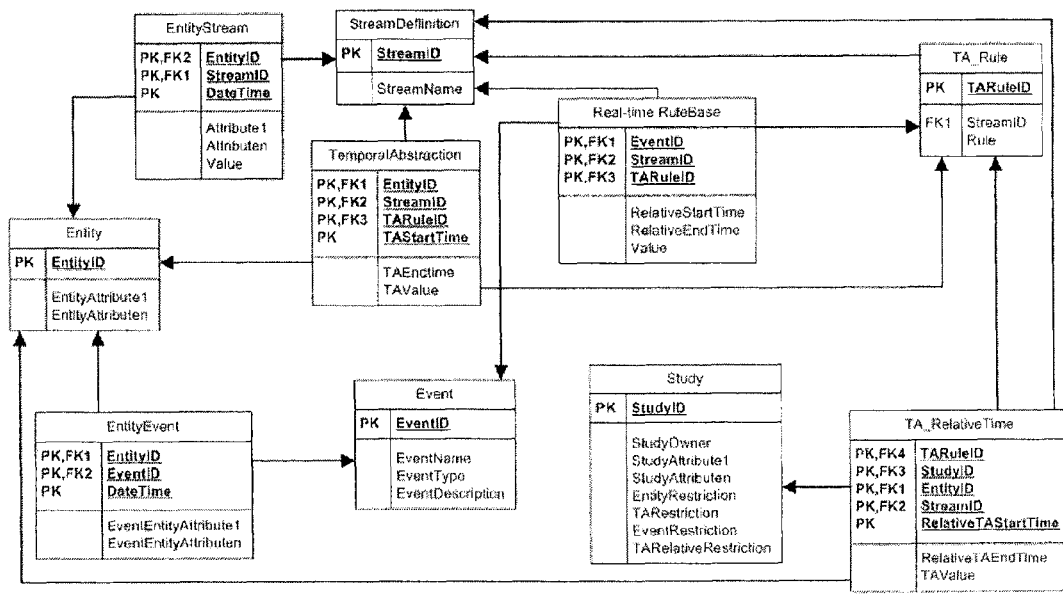
FIG. 6 illustrates a data storage schema for implementing the $STDM''_0$ framework.

FIG. 6 illustrates a data storage schema for implementing the $STDM''_0$ framework. A further example of a data storage schema as applied to support neonatal intensive care is shown in FIG. 7.

The static entity data for the entities in the framework may be recorded in an Entities table. The Entity table contains either identified or research de-identified historical clinical static data for entities. The attributes of the Entity table are EntityId, which is used to link the content of the Entities table to the content of the Entity Event, Entity Stream, Temporal-Abstraction, TA_RelativeTime and EntityDiagnosis tables. The relationship between the Entity table and the EntitySteam is one-to-many, the relationship between the Entity table and the TemporalAbstraction table is one-to-many, the relationship between the Entity table and the TA_RelativeTime table is one-to-many and the relationship between the Entity table and the EntityDiagnosis table is one-to-many. The entity table can then contain any number of EntityAttributes listed in FIG. 6 as $EntityAttribute_1$ through $EntityAttribute_n$.

As shown in FIG. 7 this can be implemented to support neonatal intensive care. Within this context, entities are patients. The entity table is shown as a patient table with a Patient_ID rather than EntityId and a series of EntityAttributes (Birthtimedate, BirthGestationalAge, Gender, BirthWeight, BirthLength, BirthHeadC).

The Event table stores definition information about the types of events that can occur to entities at a given point in time. The Event table contains the EventID code which is a unique identifier for each event together with the EventName containing a human readable name for the event. The EventType enables events to be grouped, for example, in the case where events could relate to diagnosis, recording of observations, lab results and growth recording. EventDescription contains further textual details describing what the event is.

The EntityEvent table contains a record of all events that are listed in the events table that occur to a given entity have been diagnosed with. The attributes that comprise the primary key for this table are EntityId, which may, for example, be used to link a diagnosis to a particular entity, EventID, which may, for example, used to link a record for an entity to a particular type of diagnosis, and Date and Time. A particular entity could be diagnosed with the same condition several times during the data collection process, so it may be necessary to include all of these attributes in the concatenated primary key. In FIG. 7, the Entity/Event table has been populated as a Patient/Diagnosis table, wherein the last attribute, Severity, is used to record the severity of the condition, if appropriate.

Referring back to FIG. 6, the identified or research de-identified raw sensor data for the various sensors for each entity is stored in the EntityStream table.

The attributes contained in the EntityStream table are EntityId, Stream_ID, Date and Time for the reading, a Value and a series of other Attributes, denoted as Attribute1 to Attributen as required such as but not limited to Location and Position, as set out in the clinical research schema in FIG. 7. The EntityId attribute is used to link the sensor data to the correct entity in the Entities Table. There is a many-to-one relationship between the EntityStream table and the Entities Table. The Stream_ID is used to identify which sensor and possibly within that which stream within the sensor the reading is for, and is linked to the StreamDefinition table. There is a many-to-one relationship between the EntityStream table and the StreamDefinition table.

Each stream that an entity has readings for must be identified. The StreamDefinition table contains as attributes the id, SensorId, and name, StreamName, for each stream entities may have reading values for. The SensorId is used in the EntityStream table as a foreign key to link to the StreamDefinition table to enable identification by name of each stream.

The rules for how to abstract particular streams are contained in the TA_Rule table of FIG. 6. Each stream may be linked to more than one rule to create more than one abstraction.

The attributes in the TA_Rule table are RuleID, which contains the id of a particular rule, the SensorId, which links the TA_Rule table to the StreamDefinition table, and is used to identify which type of parameter the particular rule is applied to. The Rule attribute contains the details of the particular rule. The TA_Rule table has a many-to-one relationship to the StreamDefinition table, which indicates that a particular StreamDefinition can have more than one temporal abstraction rule applied to it.

The temporal abstractions created from the entity's streams are stored in the TemporalAbstraction table. The abstractions may be created by applying previously defined abstraction rules, stored in the TA_Rule table of FIG. 6, to the data values for the individual entities' streams, which are found in the EntityStream table. The raw data for each sensor data stream for each entity is extracted from the EntityStream table, abstracted, and the resulting abstractions stored in the TemporalAbstraction table.

The attributes of the TemporalAbstraction table are EntityId, used to link a particular abstraction to a particular entity, SensorId, which is used to relate the abstraction to a particular stream, AbstractionValue (TAValue), showing the result of the abstraction (values could for example be high, low, normal, rising . . . and so on), ActualStartTime (TAStartTime), which is the time that the abstraction became true, and ActualEndTime (TAEndtime), which is the time when the particular abstraction no longer held true, it ended.

The temporal abstractions stored in this table are created by applying the rules contained in the TA_Rule table to the relevant stream of a entity, stored in the EntityStream.

The TemporalAbstraction table is linked to the Entity Table in a many-to-one relationship, indicating that a particular entity can have many abstractions stored in the table. There is a many-to-one relationship between the TemporalAbstraction table and the StreamDefinition table, which indicates that a stream can have several abstractions performed on it.

In a traditional data warehouse setting, where raw data is copied into the data warehouse and aggregated via a periodic load followed by batch aggregations, the temporal agent can be, for example, implemented as an agent in the database management system (DBMS) housing the data warehouse. This could be utilising scripts within DB2 (a trade-mark) for example. In this instance, for example, the five functions listed above would be implemented as follows:

1) Query the TA_Rule table and select all the rules from the rule column of each row of the selected rows in the table that were active.
2) Build a DB2 script that contained an insert statement for each temporal abstraction rule as listed in rule column of the TA_Rule table. The insert statement would contain the select statement that performs the temporal abstraction function for the date range specified to insert rows in to the TemporalAbstraction table.
3) Storage would be achieved by running the script and initiating the insert statements
4) Complex abstractions would select data from the newly created simple abstraction insert statements that are performed before the complex abstractions.
5) Storage of complex abstractions would be achieved by running the script and initiating the insert statements for the complex abstractions.

Within the stream computing paradigm, where data is manipulated as a stream as the data arrives in real-time, the temporal agent could be a stream computing program analysing the streams of data as the data arrives in real-time or sourcing data from the data warehouse tables and creating a series of resultant slower frequency streams that are simple or complex abstractions and then loading them in real-time in the database. In this implementation, in addition to a periodic copying of the raw data streams to the data warehouse environment, a periodic copying of the temporal abstraction data would also be required. In this instance for example, the five functions listed above would be implemented as follows in the real-time environment:

1) Use the information contained in the TA_Rule table to drive the creation of the real-time streaming modules for each rule. In IBMs Infosphere Streams for example this would result in the creation of a series of SPADE graph programs.
2) Each streaming module representing a simple abstraction would read in the source raw stream and the associated required static data and write out the resultant slower frequency output steam. These real-time streaming modules would be deployed against each entity that is being monitored by the real-time streaming environment.

3) Storage would be achieved by writing the output stream or streams to the database.

4) Similarly to 1), complex abstractions would be implemented as streaming modules that read in the created output streams from 2) from the real-time stream as it is generated or the by selecting the data once it is written to the database from the newly created simple abstractions that are performed before the complex abstractions.

5) Storage of complex abstractions would be achieved by writing the output stream or streams to the database.

The Study table of FIG. 6, which specifies a particular alignment, holds the information about any relative rules that may need to be applied to the abstractions stored in the TemporalAbstraction table for each study. Depending on a particular study undertaken, the temporal abstractions may need to be re-aligned relative to a particular point in time, such as the point of diagnosis, if the behavior of certain parameters in the time leading up to a diagnosis is to be studied. In that case the absolute point in time when a particular abstraction was true is not important, rather it is the relative point in time for each entity in relation to the entity's diagnosis time that is relevant.

There is an entry in the Study table for each study. The attributes of the Study table are Study_ID, a unique identifier for each study and used to link to the TA_RelativeTime table. The Study table could have zero to many study attributes such as but not limited to Study Name and Study Owner denoted in as the table in FIG. 6 as $StudyAttribute_1$ through $StudyAttribute_n$. The Study_Owner attribute is used to identify the user conducting the particular study. To enable the restriction, if required, of entities to those of interest, the Study table contains an attribute to define the nature of the entity restriction through the EntityRestriction attribute. To enable the restriction, if required, of events to those of interest, the Study table contains an attribute to define the nature of the event restriction through the EventRestriction attribute. To enable the restriction, if required, of temporal abstractions to those of interest, the Study table contains an attribute to define the nature of the temporal abstraction restriction through the TARestriction. To enable the restriction, if required, of relative alignments to those of interest, the Study table contains an attribute to define the nature of the relative alignment restriction through the TARelative attribute.

An example of an implementation of this table to support neonatal critical care is shown in FIG. 7 as the Study table where the Entity has been replaced with patient.

An example of the definition of a study is as follows: Researchers wish to select all patients who were born at less than 30 weeks gestation. In this example, the event of interest is episodes of neonatal bradycardia, which for the study is defined as a fall in heart rate below 10 beats per minute. The temporal abstractions of interest are 1.) the simple TAs of mean blood pressure falls below the current gestational equivalent age for more than 20 seconds; 2.) the simple TA of blood oxygen saturation falls below 85 percent for more than 20 seconds; and 3.) the complex abstraction of when 1 and 2 occur together or overlap. The relative alignment restriction is to only select temporal abstractions that occur up to 36 hour before the date and time of that neonatal bradycardia event. Of note in this example is that the same entity can have multiple events occur, resulting in multiple sets of relatively aligned data for that patient.

An example of the study restriction information as implemented in a database management system in SQL would be a series of select statement where clause components in each of the EntityRestriction, TARestriction, EventRestriction and TARelativeRestrictions attributes for restriction of rows from the Entity, TemporalAbstraction, EventRestriction and TA_Relativetime tables respectively. This could then be used in a composite insert statement to insert the data into the TA_RelativeTime table.

Referring again to FIG. 6, the TA_RelativeTime table holds the abstractions that have been realigned in time relative to a point in time that has been deemed interesting by the user who owns the study of the relatively aligned abstraction in the table. The data for multiple studies can be stored in the TA_RelativeTime table.

The attributes of the TA_RelativeTime table are very similar to the attributes in the TemporalAbstraction table, however the ActualStartTime and ActualEndTime have been replaced with RelativeStartTime and RelativeEndTime, which will be times relative to a point in time deemed interesting to the owners of the study the entry belongs to. A Study_ID attribute has been added to link the relative abstraction to a particular study in the Study table. The relationship between the TA_RelativeTime table and Study table is a many-to-one relationship, as there can be many entries in the TA_RelativeTime table that belongs to a particular study.

In this context, the relative agent can, for example, be implemented as an agent in the database management system (DBMS) housing the data warehouse. This could be utilising scripts within DB2 for example. In this instance for example, the three functions listed above would be implemented as follows:

1) Query the Study table and select all the studies and use the information contained in each column to populate the information within the resultant insert statement to create rows in the TA_RelativeTime table.

2) Build a DB2 script that contained an insert statement for each relative alignment rule as created from 1). The insert statement would contain the select statement that performs the relative alignment function for the date range specified to create rows in the TA_RelativeTime table.

3) Storage would be achieved by running the script and initiating the insert statements into the TA_RelativeTime table.

Within the stream computing paradigm, where data is manipulated as a stream as the data arrives in real-time, the relative alignment agent could be a stream computing program analysing the streams of temporal data as the data arrives in real-time or sourcing data from the data warehouse tables and creating a series of resultant slower frequency streams that are simple or complex abstractions and then loading them in real-time in the database. In this implementation, a periodic copying of the relative data would also be required to create a relative data copy for use for data mining. In this instance for example, the five functions listed above would be implemented as follows in the real-time environment:

1) Use the information contained in the Study table to drive the creation of the real-time streaming modules for each rule. In IBM InfoSphere (a trade-mark) streams for example this would result in the creation of a series of SPADE graph programs;

2) Each streaming module representing a study relative alignment would read in the temporal abstraction streams and the associated required static data and write out the resultant relatively aligned streams. These real-time streaming modules would be deployed against each entity that is considered within the scope of the particular study; and 3) Storage would be achieved by writing the output stream or streams to the database.

In addition to the above tables which form part of the STDM″$_0$ framework, the possibly resulting rules created from hypotheses that are a result of the processing in the STDM″$_0$ framework, may be stored in the Real-time Rule Base table, shown in FIG. 6, that is accessible for use by real-time patient monitoring such as the Event Stream Processor within the SMS. This table may be external to the STDM″$_0$ data store.

FIG. 6 demonstrates an example of the Real-time Rule Base table where for each EventID that has been the subject of a study, the temporal abstractions (TARuleID) related to a certain stream (StreamID) can be defined based on their relative distance from the event and where required an associated value. There can be multiple temporal abstraction rules for a stream each likely to be at different relative distances from an event. There can be multiple temporal abstractions across multiple stream for each event.

Solution Manager Service

The Solution Manager Service (SMS) is an Intelligent Decision Support System (IDSS) to support neonatal clinical management and research, in one implementation of the present invention. Interaction with the solution management service is via a series of web services. The SMS shown in FIG. 9 contains six components, in a particular representative implementation of the invention:

Solution Builder is a build-time component that captures metadata that is used to setup and initialize the runtime components and the Data Management layer.

Medical Alert Monitor is a run-time component enabling Neonatalogists to define and change complex medical alert rules.

Event Stream Processor provides a scalable data staging environment to continuously integrate and transform events to support complex medical alerts.

Analytical Processor provides a run-time interface for retrieving near real time patient data or to perform clinical trial analysis at patient or summary levels from data located in the data warehouse or real-time data store within the data management layer.

Data Management provides persistent storage of build-time metadata, medical rules and run-time physiological and clinical data stored in either the data warehouse or active rule and data store together with the temporal abstraction (TA) rule base.

Web Services Interfaces provides access to these components via a set of web services. This paper describes research relating to the Solution Manager Service and Data Collection Units.

The SMS supports both real-time processing, which in the context of the neonatal example implementation represents real-time intelligent patient monitoring, and data mining.

The STDM″$_0$ framework components as shown within FIG. 3 map to the SMS components within FIG. 8 as follows: The Clinical Log Web Service within the SMS performs the function of the Static Data Collection Web Service in the STDM″$_0$ framework.

The Physiological Log Web Service within the SMS performs the function of the Stream Data Collection Web Service in the STDM″$_0$ framework.

The Analyse Web Service within the SMS represents a set of web services in the STDM″$_0$ framework namely: Temporal Abstraction Web Service, Relative Alignment Web Service, Exploratory Data Mining Web Service, Confirmatory Data Mining Web Service and Rule Management Web Service A part of the SMS Event Stream Processor function is to enact the Processing Agent to move the data from the SMS Real-time Data Store to the SMS Data Warehouse.

The Analytical Processor within the SMS is enacted through the remaining four types of Processing Agents within the STDM″$_0$ framework namely: Temporal Agent, Relative Agent, Functional Agent and the Rules Generating Agent.

The STDM″$_0$ framework data model as shown in its generic form in FIG. 6 and an example form for neonatal intensive care in FIG. 7 is a representation of the data warehouse within the SMS.

The SMS Clinical Log Web Service and Physiological Log Web Service load data into the Real-time Data Store copy of the STDM″$_0$ framework data model Entity and EntityStream tables respectively and represent the continuously populated tables to support the real-time patient monitoring. A copy of the Temporal Abstraction table may also exist within the Real-time Data Store in the instance where the contents of this table is being created in real-time through such techniques, but not limited to, stream programming. The STDM″$_0$ framework Processing Agent as a component of the SMS Analytical Processor copies data for population within the STDM″$_0$ framework data model Entity, EntityStream and optionally the TemporalAbstraction data tables of the SMS Data Warehouse from the matching tables within the SMS Real-time Data Store as a periodic incremental load.

The SMS Medical Alert Monitor and its supporting Monitor Web Service support functions required for real-time intelligent patient monitoring.

The SMS Solution Builder and the Define Web Service can be used to initially define the tables required for the real-time intelligent patient monitoring within the SMS Real-time Data Store and the STDM″$_0$ framework data model tables within the SMS Data Warehouse.

EXAMPLES

I. Critical Care

The present invention can be implemented as a clinical monitoring and data mining environment for determining patterns related to diagnoses and, optionally, predicting future diagnoses. FIG. 8 illustrates a solution manager service for enabling clinicians to carry out the methods described above. Within the critical care context, clinical data together and physiological data are used together with temporal rules to create temporal data summary streams of the raw physiological data streams. Physiological data streams are supplemented by clinical data. These summary streams can represent summaries based on the cross correlation of multiple raw streams.

Users can easily generate individual study based relative temporal data tables in a flexible multi-dimensional environment during the data preparation step that encode the time series time stamps relative to the $t_0$ point of interest. For example, $t_0$ may refer to an alignment of neonatal patient streams for a set of neonatal patients based on the time that a certain condition was diagnosed for each patient thereby enabling alignment of preceding stream behaviors within the continuum of $t_{-1}, t_{-2}, \ldots, t_{-n}$, where n is the distance back in time of interest for a given study.

Users of the environment can create relative rules that represent a range of functions and/or criteria against the patient, event, physiological and temporal data tables.

Processing Agent

The role of the processing agent is to acquire and prepare the stream data from sensors together with static data for storage within the stream data tables and the static data tables respectively. Within the context of critical care the static data would be supplied by the clinical information systems, for example date of birth or gestational age at birth, and the stream data acquired from medical sensor devices, for example, ECG signals, or collected manually repeatedly over time, for example temperature readings taken manually repeatedly over time.

Static data can be supplied via static data web service, which in the context of critical care could be via HL7 message formats, for example. Stream data can be supplied via stream data web services.

Temporal Agent

The role of the temporal agent is to create new temporal encoded streams at a slower frequency than the data stream or streams being encoded, by abstracting the time interval, representing the trend and/or behavior of the stream during that summarized time interval. Each data stream is temporally abstracted into appropriate abstractions such as trends (increasing, decreasing) and level shifts (high, low) for example based on the temporal rules driving the temporal abstraction contained in the temporal rules table. Each raw piece of data may belong to several abstractions. For example, a particular measurement may be part of an 'increasing' abstraction, and at the same time be within 'normal' limits. Complex abstractions can also be done across multiple abstracted parameters. Each abstraction stream is stored in the temporal data table.

The relative, functional and rules generating agent may be run together as a set for any given study from $study_1$ to $study_n$. It is also possible to run the temporal agent utilising new temporal rules that are required for a particular study. This principle is illustrated via the example study below.

(a) Clinical Study Example 1: ECG Instability

A clinical researcher may be determining, for example, whether ECG instability is preceded within the past 24 hours by falls in mean blood pressure to less than gestational equivalent age (eg 35 mm Hg for a 35 weeks gestation baby) for more than 20 seconds concurrently with a fall in peripheral oxygen saturation less than 85% for greater than 20 seconds".

In this example, physiological data streams include ECG, blood pressure and peripheral oxygen saturation.

Firstly, the physiological data stream data for ECG, blood pressure and peripheral oxygen saturation is loaded into the stream data tables by the processing agent via the stream data collection web service. Similarly related clinical data is loaded into the static data table via the static data collection web service.

Through use of the temporal agent, a temporal abstraction rule may be created to create a temporally encoded stream to detect ECG instability based on assessing the ECG stream for each patient. Similarly a temporal rule may be created to determine when mean blood pressure falls below a threshold based on the patient's gestational equivalent age for a time interval of greater than 20 seconds. A temporal rule may be created to determine peripheral oxygen saturation less than 85% for greater than 20 seconds. A complex rule could be created representing where they overlap. These rules could be created using the temporal abstraction web service.

The relative agent selects patients that have been detected to have ECG instability and for this example would use the first occurrence of ECG instability to determine a time point of interest. This time point of interest is shown within FIG. 9 as the circle point of Diagnosis. Examples of where the complex temporal abstraction could have occurred are shown as the rectangular blocks over the streams that proceed the diagnosis. As can be seen in the absolute time representation in FIG. 9, the actual time points for the complex abstractions and the diagnosis of interest occur at different points in actual time for each patient.

Figure 9:
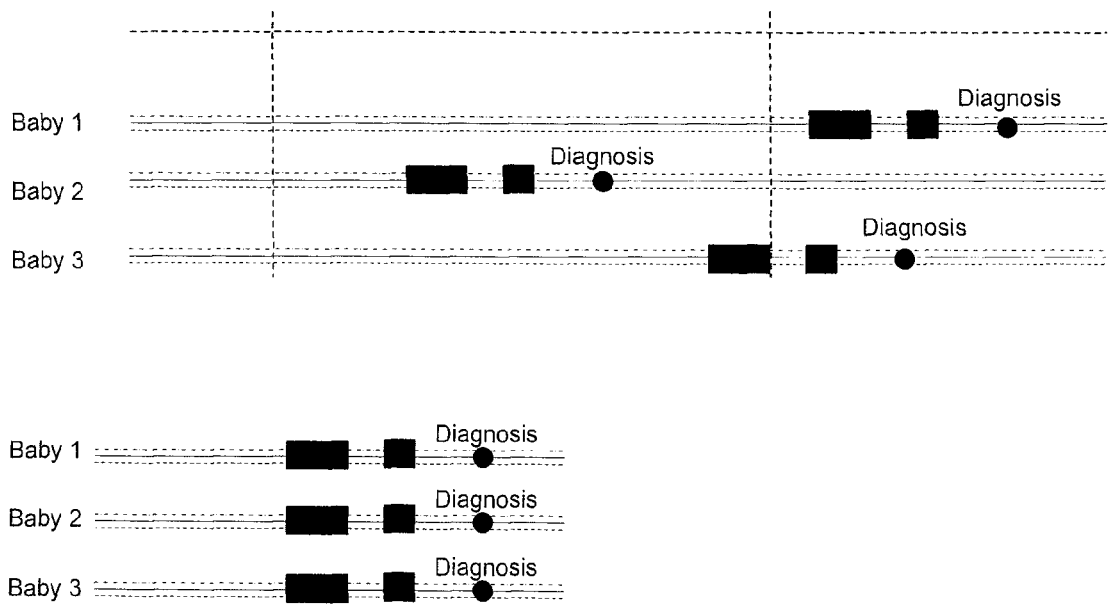
FIG. 9 illustrates a relative alignment of ECG instability streams for example.

For each selected patient the time of the ECG instability is used to reset actual times within all three streams of interest to relative times based on the time of interest becoming $t_0$, as shown in the relative time portion of FIG. 9. The example in FIG. 9 shows the similar relative distance of the episodes of the complex abstractions from the point of the diagnosis of interest for this study.

With the data prepared, temporally abstracted and aligned based on a point of interest, the two step data mining can commence. This two step process supports initial rule generation (exploratory data mining) and then testing of a null hypothesis through confirmatory data mining.

In this example, a hypothesis has already been proposed of a suspected correlation between the behavior of ECG and the preceding behavior of mean blood pressure and peripheral oxygen saturation. As a result the rule set can thus be immediately defined based on what has been proposed. However, the study could be altered to perform exploratory data mining on other data streams to see whether other temporal abstractions exist that have a high correlation of occurrence before ECG instability resulting in the need to perform exploratory data mining.

For the purposes of this example, one could encode the hypothesis such that a correlation cooefficient of 0.8 is used. This hypothesis is thus represented utilizing a correlation cooefficient notation of the form:

$$H_1: \rho_{(X,Y)} > 0.8$$

where:
X represents ECG instability and;
Y represents ABPmean<gestational age for 20 seconds; AND $SaO_2$<85% for the same 20 seconds.
The effective null hypothesis is represented as:

$$H_0: \rho_{(X,Y)} = 0.8$$

The true null hypothesis is represented as:

$$H_0: \rho_{(X,Y)} < 0.8$$

During the confirmatory data mining phase, the correlation between ECG instability with preceding ABPmean and $SaO_2$ falls is determined.

If $H_0$ cannot be accepted then the rule represented by $H_1$ above can be accepted and created as a rule within the Rulebase table. For example, the rule would be a complex abstraction based on the correlation of two simple threshold breaches of ABPmean and $SaO_2$ falls with an alert to potential for ECG stability as the rule action. The rule management web service can add, change or delete rules independent of the rules generating process. Rules can exist as production, test or development rules.

(b) Clinical Study Example 2: Mean Blood Pressure

A clinical researcher may be determining, for example, whether a correlation exists between mean blood pressure and gestational equivalent age (eg 35 mm Hg for a 35 weeks gestation baby) for babies not under treatment for diagnoses beyond those usual due to prematurity.

In this example, physiological data streams includes blood pressure.

An existing temporal rule may be utilized to determine when mean blood pressure falls below a threshold based on the patient's gestational equivalent age for a time interval of greater than 20 seconds.

The relative agent may select patients that satisfy the criteria of not being under treatment for diagnoses beyond usual due to prematurity for the duration of their $35^{th}$ gestational equivalent week. For each selected patient the time of the commencement of the $35^{th}$ week of gestational equivalent age may be used to reset actual times within the stream of interest (mean blood pressure) to relative times based on the time of interest becoming $t_0$ and moving forward for 7 days.

In this example, a hypothesis has already been proposed of a suspected correlation between the behavior of mean blood pressure and the gestational equivalent age. As a result, the rule set can thus be immediately defined based on what has been proposed.

As in the previous example a null hypothesis can be tested during the confirmatory data mining phase.

(c) Clinical Study Example 3: ECG Instability II

A clinical researcher may be determining, for example, whether ECG instability is preceded within the past 24 hours by common behaviors in physiological streams that occur for 1 minute or more.

In this example, physiological data streams include ECG and other physiological streams.

The temporal abstraction rule created previously to detect ECG instability based on assessing the ECG stream for each patient may be used. All temporal stream encodings on streams other than ECG are included in the study.

The relative agent may select patients that have been detected to have ECG instability and for this example use the first occurrence of ECG instability to determine a time point of interest. For each selected patient, the time of the ECG instability may be used to reset actual times within all streams of interest to relative times based on the time of interest becoming $t_0$.

With the data prepared, temporally abstracted and aligned based on a point of interest, the two step data mining can commence. This two step process supports initial rule generation (exploratory data mining) and then testing of a null hypothesis through confirmatory data mining.

In this example, a hypothesis has not already been proposed and hence the exploratory data mining phase is completed for a training set of patients of a suspected correlation between the behavior of ECG and the preceding behavior of other streams supplied.

If a correlation is detected on the training set, then that correlation is transformed into a null hypothesis and tested further on test data sets to determine a correlation factor.

If successful, the rule represented by $H_1$ above can be accepted and created as a rule within the rulebase data table.

II. Further Examples

The present invention can be implemented for data mining outside the field of clinical research. For example, a user may be determining a relationship between shopping patterns for two different types of products, computer network traffic characteristics before a router failure, electricity usage behaviors related to certain weather and sport events through the analysis of smart meter data, car telemetry systems information preceding a certain style of component failure within a vehicle, expected operating behaviors of a certain make and model of vehicle after a certain mileage or age, nuclear power plant operations sensor readings before equipment failure or near failure, share price purchasing trends preceding a certain share price movement behavior, or distance in time from a company announcement to a certain share price movement behavior between companies.

What is claimed is:

1. A computer implemented method for multi-dimensional temporal abstraction and data mining, the method comprising: collecting and optionally cleaning multi-dimensional data, the multi-dimensional data including a plurality of data streams, wherein the data streams include a series of sequences of events ("sequences"), and wherein across the data streams two or more of the sequences are overlapping; temporally abstracting the multi-dimensional data by one or more computer processors using a database model that is constructed to include a set of information elements that enable the processing of the data streams so as to generate dynamically a series of temporal rules for quantifying the sequences, and analyzing the behaviour of one or more predictor variables in the sequences; and relatively aligning the temporally abstracted multi-dimensional data based on an at least one time point of interest, so as to generate relatively aligned temporally abstracted multi-dimensional data across the data streams.

2. The method of claim 1, wherein the collected, temporally abstracted and relatively aligned data is stored in a data store for subsequent retrieval.

3. The method of claim 1, comprising engaging in exploratory, explanatory, or confirmatory data mining of the relatively aligned temporally abstracted multi-dimensional data.

4. The method of claim 3, comprising monitoring the data streams in real-time or near real-time in order to detect one or more events related to the predictor variables, using the dynamically constructed temporal rules.

5. The method of claim 1, comprising linking an at least one remote device to the temporally abstracted multi-dimensional data to enable further processing of the data by the at least one remote device.

6. The method of claim 1, wherein the temporal abstraction step includes the steps of retrieving an at least one temporal rule, and applying the at least one rule to the multidimensional data to create temporally abstracted multi-dimensional data.

7. The method of claim 1, wherein the temporally abstracted multi-dimensional data is characterized by a plurality of data values, each of the plurality of data values having an actual start time and an actual end time.

8. The method of claim 7, wherein the relative alignment step includes the step of calculating the difference between the actual times and the at least one time point of interest for each of the plurality of data values.

9. The method of claim 1, wherein the at least one time point of interest is an event.

10. The method of claim 1, wherein the relative alignment step includes the steps of retrieving the temporally abstracted multi-dimensional data from a data store based on selection specifications provided by a user, and applying transformations to the temporally abstracted multi-dimensional data.

11. The method of claim 1, wherein the database model are is configured to enable both the generation of the temporal rules and the execution of the temporal rules in the database model.

12. The method of claim 4, wherein the data streams are partitioned on a per variable basis, and such that whether the partitions occur in parallel or sequential form they include behaviour information based on the predictor variables so as to enable the explanation of behaviour before the point of interest.

13. A computer implemented data mining system characterized by: an at least one data store; a processor in communication with the at least one data store, the processor configured to: collect and construct from the data store an at least one time dependent data set constituting data streams wherein the data streams include a series of sequences of events ("sequences"), wherein across the data streams two or more of the sequences are overlapping, using selection criteria set by a user; apply temporal abstractions to the at least one time dependent data set in accordance with abstraction rules that are generated dynamically by a database model and that enable the quantifying of the sequences and the analyzing of behaviour of one or more predictor variables in the sequences, so as to produce an at least one temporally abstracted data set; and re-align the at least one temporally abstracted data set relative to an at least one time point of interest to produce an at least one relatively aligned data set, so as to generate temporally abstracted and relatively aligned data across the data streams.

14. The system of claim 13, wherein the at least one time dependent data set, the at least one temporally abstracted data set, and the at least one relatively aligned data set are stored for subsequent retrieval.

15. The system of claim 13, wherein the processor is further configured to engage in exploratory, explanatory, or confirmatory data mining of the at least one relatively aligned data set.

16. The system of claim 15, wherein the system enables the monitoring of the data streams in real-time or near real-time in order to detect one or more events related to the predictor variables, using the dynamically constructed temporal rules.

17. The system of claim 13, wherein the process is further configured to link an at least one remote device to the at least one temporally abstracted data set to enable further processing of the data set by the at least one remote device.

18. The system of claim 13, wherein the application of temporal abstractions includes the steps of retrieving an at least one temporal rule, and applying the at least one rule to the at least one time dependent data set to create an at least one temporally abstracted data set.

19. The system of claim 13, wherein the at least one temporally abstracted data set is characterized by a plurality of data values, each of the plurality of data values having an actual start time and an actual end time.

20. The system of claim 19, wherein re-alignment of the at least one temporally abstracted data set is characterized by calculating the difference between the actual times and the at least one time point of interest for each of the plurality of data values.

21. The system of claim 13, wherein the at least one time point of interest is an event.

22. The system of claim 13, wherein re-alignment of the at least one temporally abstracted data set is characterized by retrieving the temporally abstracted multi-dimensional data from a data store based on selection specifications provided by a user, and applying transformations to the temporally abstracted multi-dimensional data.

23. A computer readable medium having stored thereon a computer program for data mining, the computer program comprising a set of instructions for generating and storing a plurality of accessible information files when used with a processor, the set of instructions comprising a method characterized by: constructing an at least one time dependent data set constituting data streams wherein the data streams include a series of sequences of events ("sequences"), wherein across the data streams two or more of the sequences are overlapping, using selection criteria set by a user; applying temporal abstractions to the at least one time dependent data set in accordance with abstraction rules that are generated dynamically by a database model and that enable the quantifying of the sequences and the analyzing of behaviour of one or more predictor variables in the sequences, so as to produce an at least one temporally abstracted data set; relatively aligning the at least one temporally abstracted data set relative to a time point of interest to create an at least one relatively aligned data set; and storing each at least one data set for subsequent retrieval, so as to generate temporally abstracted and relatively aligned data across the data streams.

* * * * *